(12) United States Patent
Lai et al.

(10) Patent No.: US 10,473,613 B2
(45) Date of Patent: Nov. 12, 2019

(54) LIGHT-ADDRESSABLE POTENTIOMETRIC SENSING UNITS

(71) Applicant: CHANG GUNG UNIVERSITY, Taoyuan (TW)

(72) Inventors: Chao-Sung Lai, Taoyuan (TW); Chia-Ming Yang, Taoyuan (TW); Chun-Hui Chen, Zhushan Township, Nantou County (TW); Tsung-Cheng Chen, Yuanshan Township, Yilan County (TW)

(73) Assignee: CHANG GUNG UNIVERSITY, Taoyuan (TW)

( * ) Notice: Subject to any disclaimer, the term of this patent is extended or adjusted under 35 U.S.C. 154(b) by 188 days.

(21) Appl. No.: 15/237,538

(22) Filed: Aug. 15, 2016

(65) Prior Publication Data

US 2017/0176376 A1   Jun. 22, 2017

(30) Foreign Application Priority Data

Dec. 17, 2015   (TW) .................................. 104142537

(51) Int. Cl.
*G01N 27/403* (2006.01)
*G01N 27/327* (2006.01)
*G01N 27/30* (2006.01)

(52) U.S. Cl.
CPC ....... *G01N 27/4035* (2013.01); *G01N 27/305* (2013.01); *G01N 27/3275* (2013.01)

(58) Field of Classification Search
CPC ........................................ G01N 27/327–3278
USPC ..... 204/403.01–403.15; 205/777.5–778, 792
See application file for complete search history.

(56) References Cited

U.S. PATENT DOCUMENTS

| 4,963,815 | A | * | 10/1990 | Hafeman | ............. | G01N 27/305 |
|   |   |   |   |   |   | 204/403.1 |
| 6,288,527 | B1 | * | 9/2001 | Sugihara | .......... | G01N 33/48728 |
|   |   |   |   |   |   | 324/444 |
| 8,901,678 | B2 |   | 12/2014 | Chang et al. |   |   |
| 9,087,944 | B1 | * | 7/2015 | Roberts | ........... | H01L 31/035209 |

(Continued)

FOREIGN PATENT DOCUMENTS

CN      102109482 A     6/2011
TW      201516401 A     5/2015

OTHER PUBLICATIONS

Tatsuo Yoshinobu, Michael J. Schoning, Friedhelm Finger, Werner Moritz, Hiroshi Iwasaki, "Fabrication of Thin-Film Laps With Amorphous Silicon", Sensors, Oct. 30, 2004, pp. 163-169, vol. No. 4, MDPI.

(Continued)

*Primary Examiner* — Bach T Dinh
(74) *Attorney, Agent, or Firm* — Cheng-Ju Chiang

(57) ABSTRACT

Light-addressable potentiometric sensing units are provided. A light-addressable potentiometric sensing unit comprises a conductive substrate, a metal oxide semiconductor layer, and a sensing layer. The metal oxide semiconductor layer is made of indium gallium zinc oxide, indium gallium oxide, indium zinc oxide, indium oxide co-doped with tin and zinc, tin oxide, or zinc oxide. The wide-band gap characteristic of the metal oxide semiconductor layer enables the light-addressable potentiometric sensing unit to resist the interference from visible light. The light-addressable potentiometric sensing unit therefore exhibits a more stable performance.

10 Claims, 3 Drawing Sheets

(56) References Cited

U.S. PATENT DOCUMENTS

| | | | |
|---|---|---|---|
| 2002/0128234 A1* | 9/2002 | Hubbell | A61B 5/14546 514/100 |
| 2007/0207487 A1* | 9/2007 | Emig | B01J 19/0046 435/6.11 |
| 2012/0153407 A1* | 6/2012 | Chang | H01L 31/02161 257/414 |
| 2012/0187000 A1* | 7/2012 | Kahn | G01N 27/3335 205/782 |
| 2015/0060953 A1 | 3/2015 | Kunath et al. | |
| 2016/0049431 A1* | 2/2016 | Taghibakhsh | G01T 1/2006 250/370.08 |

OTHER PUBLICATIONS

Tze-Ching Fung, Chiao-Shun Chuang, Kenji Nomura, Han-Ping David Shieh, Hideo Hosono, Jerzy Kanicki, "Photofield-Effect in Amorphous In—Ga—Zn—O (a-IGZO) Thin-Film Transistors", Journal of Information Display, Dec. 2008, pp. 21-29, vol. 9, Issue No. 4, Taylor and Francis Group, LLC.

Anirban Das, Tsung-Cheng Chen, Chia-Ming Yang, Chao-Sung Lai, "A High-Speed, Flexible-Scanning Chemical Imaging System Using a Light-Addressable Potentiometric Sensor Integrated with an Analog Micromirror", Sensors and Actuators B: Chemical, Mar. 2014, pp. 225-232, Issue No. 198, Elsevier B.V.

Torsten Wagner, Carl Frederik B. Werner, Ko-Ichiro Miyamoto, Michael J. Schoning, Tatsuo Yoshinobu, "A High-Density Multi-Point LAPS Set-Up Using a VCSEL Array and FPGA Control", Sensors and Actuators B: Chemical, 2011, pp. 124-128, Issue No. 154, Elsevier B.V.

\* cited by examiner

LIGHT-ADDRESSABLE POTENTIOMETRIC SENSING UNITS

CROSS-REFERENCE TO RELATED APPLICATION AND CLAIM OF PRIORITY

This application claims the benefit of Taiwan Patent Application No. 104142537, filed on Dec. 17, 2015, in the Taiwan Intellectual Property Office, the disclosure of which is incorporated herein in its entirety by reference.

TECHNICAL FIELD

At least one embodiment of the present invention relates to a light-addressable potentiometric sensing unit. More particularly, a light-addressable potentiometric sensing unit comprising a metal oxide semiconductor layer made of indium gallium zinc oxide (IGZO), indium gallium oxide (IGO), indium zinc oxide (IZO), indium oxide co-doped with tin and zinc (ITZO), tin oxide ($SnO_2$), or zinc oxide (ZnO) and a sensing layer made of niobium oxide ($NbO_x$), hafnium oxide ($HfO_2$), hafnium oxynitride (HfON), silicon nitride ($Si_3N_4$), titanium oxynitride (TiON), titanium nitride (TiN) or tantalum oxide ($Ta_2O_5$).

DESCRIPTION OF THE RELATED ART

A light-addressable potentiometric sensor (LAPS) is a sensor that uses light to scan the variation in concentration and obtain 2-D images. The LAPS comprises an electrolyte-insulator-semiconductor (EIS) structure, and usually is used as bio-sensors based on the properties including the short reaction time and high sensitivity to ions.

The LAPS technique is commonly used to measure and analyze ions and chemicals in areas of chemistry and biochemistry. A technician may evaluate the progress of reactions by reading the change in ion concentrations, presented as images and other optical means, obtained by the LAPS technique.

However, the light-addressable potentiometric sensing unit is highly sensitive to light. The measurement based on EIS is significantly affected and interfered by ambient lighting. Therefore, the measurement is usually performed in a darkroom.

Even with a darkroom, the accuracy and stability of the test is interfered by visible light if the technician provides insufficient protection from a minor leakage of visible light into the darkroom.

SUMMARY

At least one embodiment of the present invention provides a light-addressable potentiometric sensing unit to suppress the aforementioned problems. The light-addressable potentiometric sensing unit comprises a conductive substrate, a metal oxide semiconductor layer, and a sensing layer. The conductive substrate is disposed on a substrate, wherein the metal oxide semiconductor layer is disposed on the conductive substrate and the sensing layer is yet further disposed on the metal oxide semiconductor layer. The metal oxide semiconductor layer is made of one selected from the group consisting of indium gallium zinc oxide (IGZO), indium gallium oxide (IGO), indium zinc oxide (IZO), indium oxide co-doped with tin and zinc (ITZO), tin oxide ($SnO_2$), and zinc oxide (ZnO).

DESCRIPTION OF THE PREFERRED EMBODIMENTS

Figure 1:
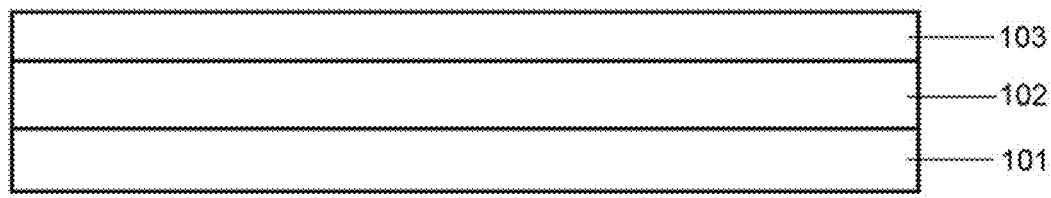
FIG. 1 is a schematic diagram illustrating a light-addressable potentiometric sensing unit, according to some embodiments of the present invention.

The examples depicted in the following section are provided for the purpose of detailed explanation of the features of preferred embodiments, in order to enable one having ordinary skill in the art to understand the preferred embodiments. It is to be understood that the thicknesses and ratios provided in the drawings are merely for the purposes of illustration and that various changes without departing from the spirit and intention may be included in the present invention.

FIG. 1 is a schematic diagram illustrating a light-addressable potentiometric sensing unit, according to some embodiments of the present invention. As illustrated in FIG. 1, the light-addressable potentiometric sensing unit 100 in the present embodiments comprises a conductive substrate 101, a metal oxide semiconductor layer 102, and a sensing layer 103. More particularly, the metal oxide semiconductor layer 102 is formed on the conductive substrate 101, and the sensing layer 102 is further formed on the metal oxide semiconductor layer 102.

In the embodiments of FIG. 1, the conductive substrate 101 is deposited on one selected from the group consisting of a glass, a ceramic, and a plastic. The conductive substrate is made of one selected from the group consisting of indium tin oxide (ITO), fluorine doped tin oxide (FTO), tin oxide ($SnO_2$), zinc oxide (ZnO), poly(3,4-ethylenedioxythiophene) (PEDOT), silver nano-wires, metal nano-particles, carbon nanotubes (CNT), and graphene. In some preferred embodiments, the conductive substrate is made of ITO and is deposited on a glass.

Moreover, the metal oxide semiconductor layer 102 is made of one selected from the group consisting of indium gallium zinc oxide (IGZO), indium gallium oxide (IGO), indium zinc oxide (IZO), indium oxide co-doped with tin and zinc (ITZO), tin oxide ($SnO_2$), and zinc oxide (ZnO). The sensing layer 103, on the other hand, is made of one selected from the group consisting of niobium oxide ($Nb_xO_y$), hafnium oxide ($HfO_2$), hafnium oxynitride (HfON), silicon nitride ($Si_3N_4$), titanium oxynitride (TiON), titanium nitride (TiN) and tantalum oxide ($Ta_2O_5$). In some preferred embodiments, the metal oxide semiconductor layer 102 and the sensing layer 103 are made of IGZO and $NbO_x$ respectively.

The conductive substrate 101 in some embodiment of FIG. 1 is made of ITO, and the conductive substrate 101 is cleaned with methanol and acetone before deposit the metal oxide semiconductor layer 102 thereon. The metal oxide semiconductor layer 102 is made of IGZO, in which the atomic ratio of In:Ga:Zn:O, each is in 99.9% purity, is 1:1:1:4.

The deposition is performed by RF reactive magnetron sputtering. The condition for the RF reactive magnetron sputtering is set at a power of 200 W and a temperature of 250° C. under a mixture flow of Ar and $O_2$. The ratio of Ar:$O_2$ is 24:1 in the mixture flow. The metal oxide semiconductor layer 102 formed by the RF reactive magnetron sputtering has a thickness of 350 nm measured by a polarimeter.

The sensing layer 103 is also formed on the metal oxide semiconductor layer 102 by deposition. The sensing layer 103 in the embodiments is made of $Nb_xO_y$. More particularly, the 99.9% pure Nb sputtering target is sputtered under a power of 200 W and then introduced to an Ar gas flow (20 sccm) and an $O_2$ gas flow (5 sccm) sequentially to formed the sensing layer 103. The sensing layer 103 has a thickness of 45 nm.

Figure 2:
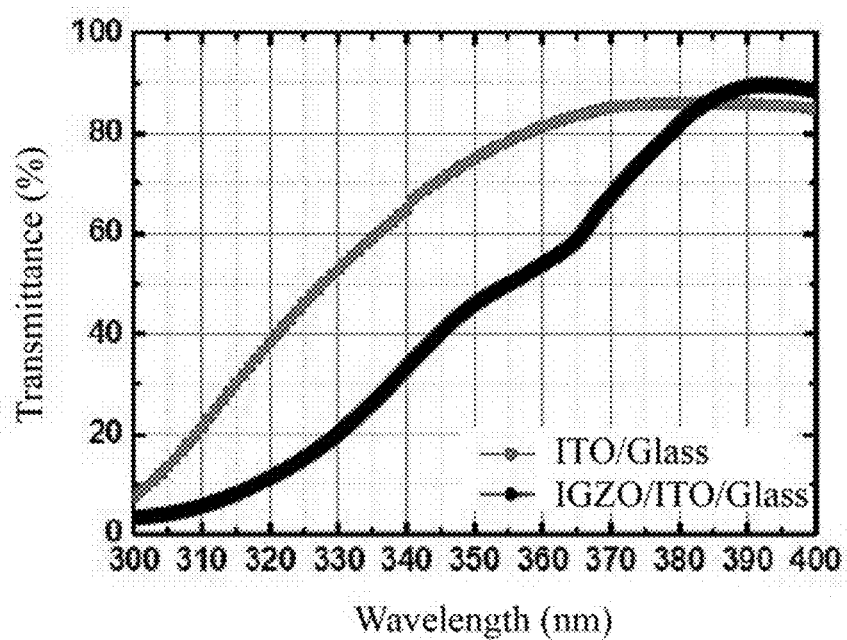
FIG. 2 is a chart illustrating the transmittance over wavelength, according to some embodiments of the present invention.

FIG. 2 is a chart illustrating the transmittance over wavelength, according to some embodiments of the present invention. The test is based on a metal oxide semiconductor layer 102 made of IGZO and a conventional ITO/glass substrate. The metal oxide semiconductor layer 102 exhibits a lower transmittance in the 300-380 nm region, which indicates that the metal oxide semiconductor layer 102 has high absorbency of ultraviolet (UV) light and may effectively convert the UV light into photovoltage. The metal oxide semiconductor layer 102 allows most non-UV light to pass through, which is evidenced by the transmittance in the above 380 nm region. Accordingly, the source of photovoltage is mostly from UV light instead of visible light. The light-addressable potentiometric sensing unit 100 in the embodiments is therefore able to resist the interference from visible light, because most of the visible light is not absorbed and converted into photovoltage.

Figure 3:
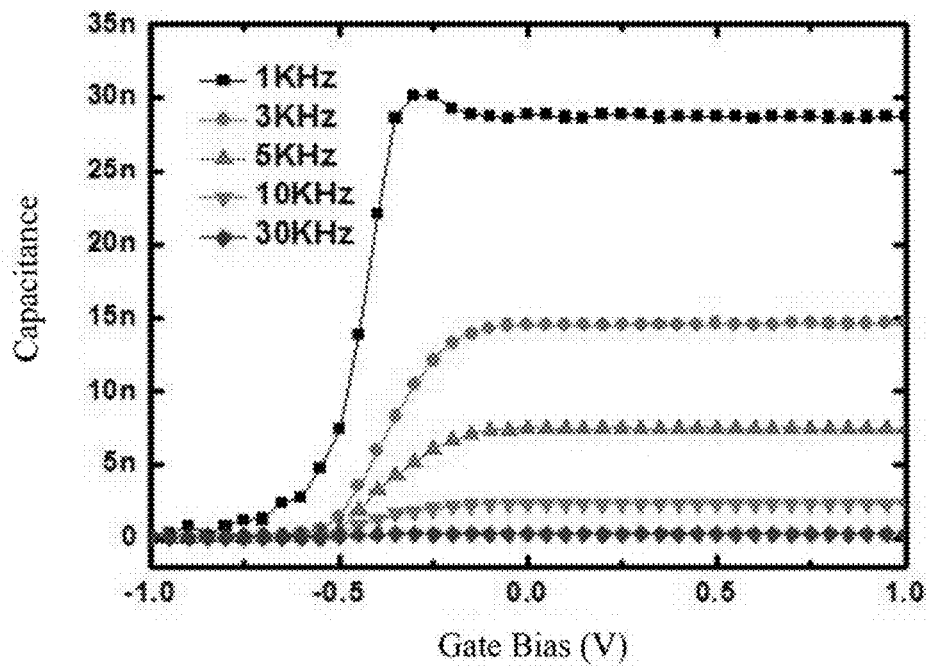
FIG. 3 is a chart illustrating the C-V profiles for difference wavelengths, according to some embodiments of the present invention.

FIG. 3 is a chart illustrating the C-V profiles for difference wavelengths, according to some embodiments of the present invention. As shown in FIG. 3, the maximum value of the C-V measurement is at 10 KHz, in accordance to the light-addressable potentiometric sensing unit in some embodiments.

Figure 4:
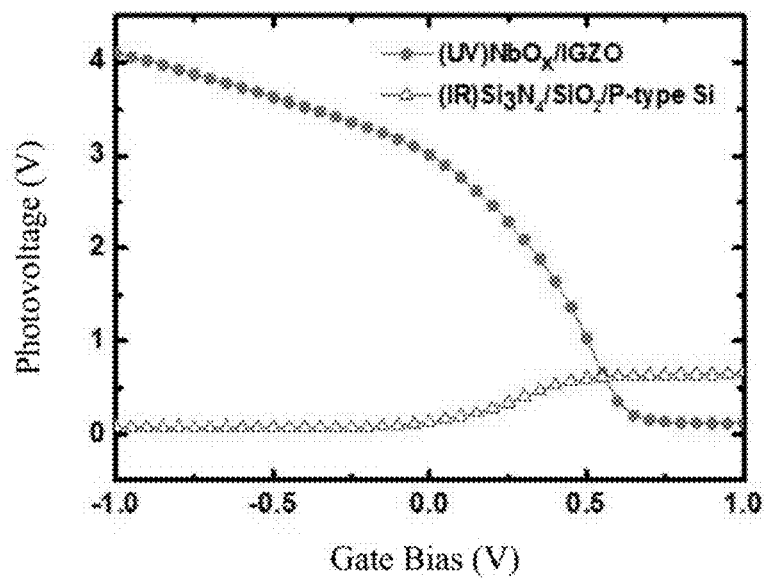
FIG. 4 is a chart illustrating the photovoltage obtained by difference materials, according to some embodiments of the present invention.

FIG. 4 is a chart illustrating the photovoltage obtained by difference materials, according to some embodiments of the present invention. The first material in FIG. 4 is a combination of a sensing layer 103 made of $NbO_x$ and a metal oxide semiconductor layer 102 made of IGZO, in accordance with one embodiment of the present invention. The second material in FIG. 4 is a conventional $Si_3N_4/SiO_2$/P-type Si material. As shown in FIG. 4, the first material exposed to UV light generated a photovoltage five times higher than the photovoltage generated by the second material under the exposure to IR light.

Figure 5:
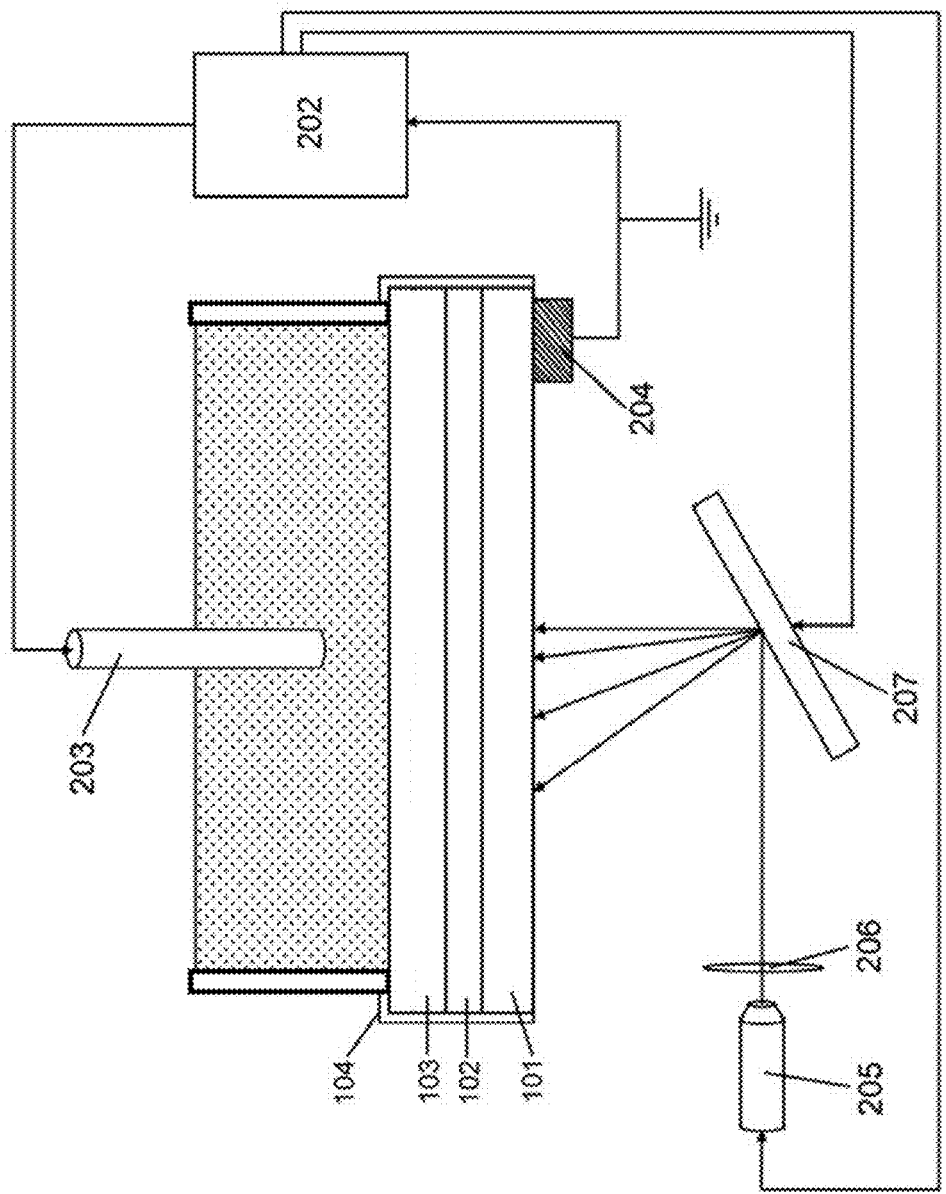
FIG. 5 is a schematic diagram illustrating a light-addressable potentiometric sensor, according to some embodiments of the present invention.

FIG. 5 is a schematic diagram illustrating a light-addressable potentiometric sensor, according to some embodiments of the present invention. As illustrated in FIG. 5, the light-addressable potentiometric sensor 200 comprises a sensing area (i.e., the contact area between the sample solution illustrated in dots and the sensing layer 103), a reference electrode 203, a working electrode 204, a light-emitting module, and a processor module 202.

The sensing area is disposed on the sensing layer 103, and further surrounded by a packaging material 104. The packaging material 104 is made of one selected from the group consisting of epoxy, silicone, polydimethylsiloxane (PDMS), and polycarbonate. More specifically, the packaging material 104 is made of PDMS in the embodiment of FIG. 5, but it is to be understood that the present invention is not limited thereto. The sample solution (illustrated in dots in FIG. 5) contacts with the sensing layer 103 as the sample solution is injected. The reference electrode 203 is disposed to the sensing area and the working electrode 204 is connected to the light-addressable potentiometric sensing unit.

The sensing area is configured to detect the concentration of an ion or a biological molecule in a sample solution (illustrated in dots in FIG. 5). The ion is one selected from the group consisting of $H^+$, $OH^-$, $K^+$, $Na^+$, $Ca^{2+}$, and $Cl^-$, whereas the biological molecule is one selected from the group consisting of proteins, lipids, saccharides, antigens, antibodies, ribonucleic acids (RNA), and deoxyribonucleic acids (DNA). However, it is to be understood that the present invention is not limited thereto.

The light-emitting module is configured to provide light to the bottom surface of the light-addressable potentiometric sensing unit 100. More particularly, the light-emitting module comprises a light-emitting unit 205, a light-focusing unit 206, and a light-reflecting unit 207, in which the light-focusing unit 206 is disposed between the light-emitting unit 205 and the light-reflecting unit 207. And the processor module 202 is connected with the light-emitting unit 205 and the light-reflecting unit 207 respectively.

The light-emitting unit 205 is one selected from the group consisting of a light-emitting diode (LED), an organic light-emitting diode (OLED), a laser diode (LD), and an electroluminescence (EL) element. In some preferred embodiments, the light-emitting unit 205 is an EL generating laser beam, the light-focusing unit 206 is a convex lens, and the light-reflecting unit 207 is a micromirror; however, the present invention is not limited thereto. On the other hand, the processor module 202 is a field-programmable gate array (FPGA) and may be connected with a variety of controllers and modules based on design considerations.

As in some embodiments, the processor module comprises a controller, a function generator, an amplifier, a filter, a DAQ-card, and an industrial computer or a computer for computations. The controller is a microcontroller or a programmable logic controller, and is connected with the light-reflecting unit 207 in order to control the movement of the light-reflecting unit 207 through controlling a micro motor. The function generator is connected with the light-emitting unit 205 to controller the frequency, power, and other parameters of the light outputted by the light-emitting unit 205. The amplifier, the filter, the DAQ-card, and the industrial computer or the computer for computation are configured to receive, compute, or store the detected data.

In the embodiments of FIG. 5, the processor module 202, a FPGA platform, coordinates the operations of modules. The light-emitting unit 205 emits a laser beam in accordance with the command from the function generator. The laser beam is focused by the light-focusing unit 206 and then reflected by the light-reflecting unit 207. At the same time, the processor module 202 sends out movement commands through the controller to the light-reflecting unit 207. The light-reflecting unit 207 receives the movement commands then adjusts its angle to reflect the laser beam from the light-emitting unit 205 to the bottom surface of the light-addressable potentiometric sensing unit.

The sensing layer 103 exhibits different surface potentials based on the concentrations of ions and pH in the sample solution. Under the DC bias voltage applied from the reference electrode 203 in the sample solution and the working electrode 204 connected to the light-addressable potentiometric sensing unit 100, different photocurrents and photovoltages are therefore generated as the laser beam is reflected from the light-reflecting unit 207 to the light-addressable potentiometric sensing unit 100. The change in photocurrent flowing between the working electrode 204 and the reference electrode 203 is measured and transmitted to the amplifier, the filter, the DAQ-card, and the industrial computer or computer in the process module 202 to calculate the change in ion concentration and pH in the sample solution.

An image may be generated according to the method in the embodiments. The photovoltage and photocurrent of each region targeted by the laser beam are measured, recorded, and converted into colored pixels and then plugged into a grid. The grid then forms an image reflecting the path of the laser beam emitted from the light-reflecting unit 207 configured by a user.

The embodiments of FIG. 5 use the FPGA platform to coordinate the light-emitting unit 205, the light-reflecting unit 207, and the processor module 202 and process the data obtained from the light-addressable potentiometric sensing unit. The embodiments therefore elevate the accuracy and reduce the processing time to collect, compile, and organize data.

Accordingly, some embodiments of the present invention provide a light-addressable potentiometric sensing unit 100 and a light-addressable potentiometric sensor having thereof. These embodiments exhibit superior efficiency in producing photocurrent and photovoltage and stronger resistance to visible light as compared to conventional materials. Furthermore, these embodiments cooperate with synchronizing systems to coordinate the measuring, reading/writing, and saving processes to largely reduce the time on obtaining data as well as increase the accuracy.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A light-addressable potentiometric sensing unit, comprising:
    a conductive substrate, wherein the conductive substrate is made of indium tin oxide (ITO) and is deposited on a glass;
    a metal oxide semiconductor layer disposed on the conductive substrate, wherein the metal oxide semiconductor layer is made of indium gallium zinc oxide (IGZO); and
    a sensing layer disposed on the metal oxide semiconductor layer, wherein the sensing layer is made of niobium oxide ($NbO_x$);
    wherein the metal oxide semiconductor layer absorbs 80% ultraviolet light at 330 nm, and converts the ultraviolet light into photo-voltage in 300-380 nm.

2. The light-addressable potentiometric sensing unit as claimed in claim 1,
    wherein the metal oxide semiconductor layer has a thickness of 350 nm.

3. The light-addressable potentiometric sensing unit as claimed in claim 1,
    wherein the sensing layer has a thickness of 45 nm.

4. A light-addressable potentiometric sensor, comprising:
    the light-addressable potentiometric sensing unit as claimed in claim 1;
    a working electrode connected to the light-addressable potentiometric sensing unit;
    a sensing area disposed on the sensing layer, wherein the sensing area is surrounded by a packaging material;
    a reference electrode disposed to the sensing area;
    a light-emitting module configured to provide light to the bottom surface of the light-addressable potentiometric sensing unit, wherein the light-emitting module comprises:
        a light-emitting unit;
        a light-reflecting unit; and
        a light-focusing unit disposed between the light-emitting unit and the light-reflecting unit; and
    a processor module connected to the working electrode, the reference electrode, the light-emitting unit, and the light-reflecting unit respectively.

5. The light-addressable potentiometric sensor as claimed in claim 4,
    wherein the light-emitting unit is one selected from the group consisting of a light-emitting diode (LED), an organic light-emitting diode (OLED), a laser diode (LD), and an electroluminescence (EL) element.

6. The light-addressable potentiometric sensor as claimed in claim 4,
    wherein the packaging material is made of one selected from the group consisting of epoxy, silicone, polydimethylsiloxane, and polycarbonate.

7. The light-addressable potentiometric sensor as claimed in claim 4,
    wherein the processor module is a field-programmable gate array (FPGA), and
    wherein the processor module comprises:
    a controller connected with the light-reflecting unit;
    a function generator connected with the light-emitting unit.

8. The light-addressable potentiometric sensor as claimed in claim 4,
    wherein the sensing area is configured to detect the concentration of an ion or a biological molecule in a sample solution.

9. The light-addressable potentiometric sensor as claimed in claim 8,
    wherein the biological molecule is one selected from the group consisting of proteins, lipids, saccharides, antigens, antibodies, ribonucleic acids (RNA), and deoxyribonucleic acids (DNA).

10. The light-addressable potentiometric sensor as claimed in claim 8,
    wherein the ion is one selected from the group consisting of $H^+$, $OH^-$, $K^+$, $Na^+$, $Ca^{2+}$, and $Cl^-$.

* * * * *